United States Patent
Malhotra et al.

(10) Patent No.: US 12,324,811 B2
(45) Date of Patent: Jun. 10, 2025

(54) INTRANASAL FORMULATION

(71) Applicant: CIPLA LIMITED, Mumbai (IN)

(72) Inventors: Geena Malhotra, Mumbai (IN); Sarabjit Singh, Thane (IN); Kalindi Gandhi, Mumbai (IN); Vipul Mittal, Thane (IN)

(73) Assignee: CIPLA LIMITED, Mumabi (IN)

( * ) Notice: Subject to any disclaimer, the term of this patent is extended or adjusted under 35 U.S.C. 154(b) by 1000 days.

(21) Appl. No.: 17/415,966

(22) PCT Filed: Dec. 18, 2019

(86) PCT No.: PCT/IN2019/050932
§ 371 (c)(1),
(2) Date: Jun. 18, 2021

(87) PCT Pub. No.: WO2020/129085
PCT Pub. Date: Jun. 25, 2020

(65) Prior Publication Data
US 2021/0379080 A1    Dec. 9, 2021

(30) Foreign Application Priority Data

Dec. 18, 2018 (IN) .............................. 201821047778

(51) Int. Cl.
*A61K 31/5517* (2006.01)
*A61K 9/00* (2006.01)
*A61K 47/18* (2017.01)
*A61K 47/26* (2006.01)

(52) U.S. Cl.
CPC ........ *A61K 31/5517* (2013.01); *A61K 9/0043* (2013.01); *A61K 47/183* (2013.01); *A61K 47/186* (2013.01); *A61K 47/26* (2013.01)

(58) Field of Classification Search
CPC .............. A61K 31/5517; A61K 9/0043; A61K 47/183; A61K 47/186; A61K 47/26
See application file for complete search history.

(56) References Cited

U.S. PATENT DOCUMENTS

| | | | |
|---|---|---|---|
| 7,700,588 B2 | 4/2010 | Merkus | |
| 2008/0275030 A1* | 11/2008 | Gizurarson | A61K 9/0043 514/772.3 |

FOREIGN PATENT DOCUMENTS

| IN | 201821047778 | 12/2018 | |
|---|---|---|---|
| WO | WO-9513810 A1 * | 5/1995 | ........... A61K 31/415 |
| WO | 2001030391 A2 | 5/2001 | |
| WO | 02089768 A1 | 11/2002 | |
| WO | 2005089768 A1 | 9/2005 | |
| WO | WO-2009046444 A2 * | 4/2009 | ......... A61K 31/5513 |
| WO | 2012174158 A2 | 12/2012 | |
| WO | 20120174158 A1 | 12/2012 | |
| WO | WO-2014158119 A1 * | 10/2014 | ......... A61K 31/4174 |
| WO | WO-2016102984 A1 * | 6/2016 | ......... A61K 31/4174 |
| WO | 2020129085 A1 | 6/2020 | |

OTHER PUBLICATIONS

Botner et al. "Intranasal Delivery of Two Benzodiazepines, Midazolam and Diazepam, by a Microemulsion System". Pharmacology & Pharmacy, 2:180-188 (Year: 2011).*

Gudmundsdottir, H., et al., "Intranasal administration of midazolam in a cyclodextrin based formulation: pioavailability and clinical evaluation in humans", Pharmazie, Dec. 2001, 963-6, 56(12), AVOXA—Mediengruppe Deutscher Apotheker GmBH, Eschborn, Deutschland.

Knoester, P. D., et al., "Pharmacokinetics and pharmacodynamics of midazolam administered as a concentrated Intranasal spray. A study in healthy volunteers", British Journal of Clinical Pharmacology, May 2, 2002, 501-7, 53(5), Blackwell Science Ltd, United Kingdom.

Wilton, Niall C.T., et al., "Preanesthetic Sedation of Preschool Children Using Intranasal Midazolam", Anesthesiology: Clinical Reports, Dec. 1988, 972-5, 69(6).

Foreign communication from a related application—International Search Report and Written Opinion of the International Searching Authority of International Application No. PCT/IN2019/050932, dated Mar. 19, 2020, 8 pages.

Foreign communication from a related application—International Preliminary Report on Patentability of International Application No. PCT/IN2019/050932, dated Jun. 16, 2021, 6 pages.

Foreign communication from a related application—EP Examination Report, EP Application No. 19836599.1 dated Jul. 22, 2024, 5 pages.

* cited by examiner

*Primary Examiner* — Jeffrey S Lundgren
*Assistant Examiner* — Ibrahim D Bori
(74) *Attorney, Agent, or Firm* — Conley Rose, P.C.; Rodney B. Carroll (57) ABSTRACT

The present invention relates to the formulation of midazolam. In particular, the invention provides new midazolam formulation for intranasal administration. These formulations contain midazolam in a high concentration from about 1% to about 10% w/w of the formulation and process of preparation thereof.

13 Claims, 2 Drawing Sheets

INTRANASAL FORMULATION

CROSS REFERENCE TO RELATED APPLICATIONS

This application is a filing under 35 U.S.C. 371 as the National Stage of International Application No. PCT/IN2019/050932 filed Dec. 18, 2019 and entitled "Intranasal Formulation," which claims priority to Indian Provisional Patent Application Serial Number 201821047778 filed on Dec. 18, 2018, both of which are incorporated herein by reference, in their entirety.

FIELD OF INVENTION

The present invention relates to formulations of midazolam. In particular, the invention provides improved midazolam formulations for intranasal administration comprising high concentrations of midazolam. There is also provided a process of preparing the formulation and the use of the said formulation thereof in the treatment and/or prevention of repeated seizures and lower the risk of generalized tonic-clonic seizures in hospitalized epilepsy patients.

BACKGROUND OF INVENTION

Midazolam is a potent short-acting benzodiazepine derivative with an imidazole structure and with anxiolytic, amnestic, hypnotic, anticonvulsant, sedative and muscle relaxant pharmacological properties. It is a white to light yellow crystalline compound, insoluble in water. Because of the basicity of this molecule, it is possible to prepare salts (e.g., with hydrochloric, maleic and lactic acid) which are soluble in water. From these salts, stable aqueous solutions with a pH of 3.5 can be made for intravenous and intramuscular injections of midazolam. Midazolam, its salts and various compositions have been described extensively in patent and non-patent literature. Chemically, midazolam HCl is 8-chloro-6-(2-fluorophenyl)-1-methyl-4H-imidazo[1,5-a][1,4]benzodiazepine hydrochloride. Midazolam hydrochloride has the following structural formula:

Midazolam is metabolized into an active metabolite alpha1-hydroxymidazolam. Age-related deficits, renal and liver status affect the pharmacokinetic factors of midazolam as well as its active metabolite. However, the active metabolite of midazolam is minor and contributes to only 10% of biological activity of midazolam. Midazolam is poorly absorbed orally, with only 50% of the drug reaching the bloodstream and has low peak plasma concentrations. It is extensively degraded by first-pass elimination and has also been found to be a substrate for the intestinal drug efflux transporter. Such disadvantages are also observed when midazolam is administered rectally. Thus, for midazolam, oral route of administration is not suitable.

Following administration by injection, midazolam is characterized by a fast onset of action as well as short duration of action, due to its rapid metabolic inactivation by liver enzymes. Midazolam is metabolised by cytochrome P450 (CYP) enzymes and by glucuronide conjugation. The therapeutic as well as adverse effects of midazolam are due to its effects on the $GABA_A$ receptors; midazolam does not activate $GABA_A$ receptors directly but, as with other benzodiazepines, it enhances the effect of the neurotransmitter GABA on the $GABA_A$ receptors (increase frequency of Cl− channel opening) resulting in neural inhibition. Almost all of the properties can be explained by the actions of benzodiazepines on $GABA_A$ receptors. However, this mode of administration has a number of disadvantages such as the injections are painful and not well accepted by the patients, particularly by young children.

An alternative mode of administration which can overcome the disadvantages of other routes of administration i.e. oral and parenteral is intranasal route of administration. The advantages of intranasal route of administration is that it is painless, has better patient compliance, does not require sterile technique, intravenous catheters or other invasive devices, and it is immediately and readily available for all patients, and rapid drug absorption as it avoids hepatic first-pass elimination. The rich vascular plexus of the nasal cavity provides a direct route into the blood stream for medications that easily cross mucous membranes. Also, the mucosa of the nasal cavity is constructed from a highly vascularized tissue covered by an epithelium with numerous microvilli. It has a much higher permeability than other mucosal surfaces, including the sublingual area, various regions of the gastrointestinal tract, and the buccal mucosa. In addition, nasal administration of drugs results in pharmacokinetic and pharmacodynamic profiles, which are very similar to those observed after intravenous injections.

However, the major problem associated with intranasal drug administration is the fact that most drug molecules diffuse poorly and slowly through the nasal mucosal membrane and thus the desired levels of the therapeutic agent cannot be achieved by means of simple transnasal administration. An additional constraint concerning nasal administration is that administration is limited to a small volume, i.e. it is generally not possible to administer more than approximately 150 mL per nostril. Volumes of formulation above this level will drain out into the pharynx and be swallowed. Hence, it is necessary that the required dose of the drug is provided in such a volume.

Thus, in general, it is difficult to formulate nasal formulation of drugs. Still, some attempts have been made to provide midazolam formulations administered by nasal route. Several literatures demonstrate the beneficial effects of intranasally administered midazolam in patients, both in children and adults. When administered in this way, midazolam appears to have a rapid onset of action (about 10 minutes) and a relatively short duration of action (30 to 60 minutes). Preanesthetic sedation of preschool children using intranasal midazolam at dosages of 0.2 mg/kg is disclosed in Wilson et. al; Anesthesiology. 1988 December; 69(6): 972-5.

WO2005/089768 discloses a pharmaceutical composition for intranasal administration comprising an effective amount of a benzodiazepine or pharmaceutically acceptable salt thereof, a nasal carrier; and at least one or more sweeteners, flavoring agents, or masking agents or combinations thereof. It further discloses pharmaceutical composition for intranasal administration comprising an effective amount of midazolam or pharmaceutically acceptable salt thereof, polyethylene glycol, saccharin powder, and propylene glycol.

WO 01/30391 discloses a pharmaceutical composition for transmucosal delivery comprises an aqueous solution of an inclusion complex of midazolam and a water-soluble substituted beta-cyclodextrin. The solution contains from 2 to 20 mg/ml of midazolam and has a pH of from 4 to 7.

Thus, although attempts have been made to formulate nasal formulations of midazolam, unfortunately, nasal delivery of midazolam has not been very successful until now. One of the reasons of this failure may be the absence of solvents that are able to dissolve midazolam at efficacious dosages without leading to nasal mucosal damage. The maximal volume of nasal application is ideally restricted to approximately 100 μL requiring the efficacious dose of midazolam to be dissolved within this volume. Higher volumes lead to nasal drop-off or swallowing, which in turn may lead to gastrointestinal absorption followed by first-pass metabolism resulting in lower and unpredictable concentrations, a high variability in midazolam bioavailability, and a relatively long onset of action. This in turn can cause overdosing if a second dose is applied because the first one did not act fast enough. The most concentrated form of the midazolam injection fluid only contains 5 mg ml$^{-1}$. As a result, for conscious sedation, at least 1 ml (=5 mg midazolam) needs to be administered intranasally, a volume that is 10 times larger than the nasal mucosa can receive and retain. This therefore leads to leakage and/or swallowing of the fluid, which in turn leads to inaccurate and inadequate dosing. Also, the nasal administration of such large volumes of solution also leads to a number of unpleasant side-effects such as lacrimation, burning sensations, irritation in the nose and throat, and general discomfort. A further problem is clearly the loss of a large proportion of the composition and of the midazolam, which leads to inconsistent and unpredictable amounts of midazolam being absorbed.

It is therefore clear that the use of commercially available midzolam injection solutions for intranasal administration is inefficient and unpleasant for the patients, due to the necessary large volumes applied. This can lead to reduced nasal bioavailability and ineffective plasma peak concentrations of midazolam and therefore to an insufficient therapeutic efficacy. For efficient and comfortable nasal drug delivery, volumes of about 200 μl (100 μl into each nostril) are normally the maximum that should be administered to a patient. This implies that there is an urgent need for the availability of nasal formulations with highly increased midazolam concentrations in comparison with the midazolam injection solutions. A few nasal midazolam formulations have been developed which comprises high midazolam content and also seek to reduce the total volume of liquid to be delivered intranasally to the patients.

The nasal formulation used by Loftsson et al. (2001) disclosed in Pharmazie. 2001 December; 56(12):963-6 is comprises midazolam hydrochloride (17 mg/ml) with high concentration (14%) of Captisol® sulfobutylether-[3-cyclodextrin sodium salt (SBEBCD; and 0.1% hydroxypropyl methylcellulose as solubilizer, 0.02% benzalkonium chloride and 0.1% EDTA as preservatives in an acidic solution at pH 4.3. However, cyclodextrin are also absorbed themselves and in studies reported in literature of the past, it is observed that high concentration of cyclodextrin can cause severe damage to nasal mucosa, inducing gross tissue damage and not keeping the histological integrity of the nasal mucosa.

The intranasal midazolam formulation used by Knoester et al. (2002a, 2002) and Tenk et al. (2003) consists of midazolam hydrochloride (30.9 mg/ml) in a mixture of 25% (v/v)propylene glycol and Water (pH 4). It also contains 1% (v/v) benzyl alcohol as a preservative. A dose of 5 mg midazolam base is delivered by two sprays of 90 pl and, for a dose of 10 mg midazolam base, 4 sprays of 90 pl are needed (providing a total dose of 360 pl). The use of this formulation for intranasal midazolam administration in healthy volunteers and in epilepsy patients, providing a dose of 5 mg or 10 mg (90-180 pl in each nostril), causes nasal irritation, lacrimation and irritation of the throat in almost all subjects, as well as a bitter taste. Also, this midazolam formulation has been shown to be Damaging to nasal membrane probably due, in particular, to the presence of 25% propylene glycol and 1% benzyl alcohol. It is evident from these studies that the volume of the formulation used to administer a dose of 5 and 10 mg via the nose is very large (two and four nasal sprays), and this is probably the cause of many of these adverse side effects. These adverse effects could prohibit the use of this formulation in clinical practice.

U.S. Pat. No. 7,700,588 provides pharmaceutical composition for intranasal administration, comprising midazolam in a concentration of from 35 mg/ml to 100 mg/ml; a solubilizer comprising at least one of propylene glycol, glycerol, polyethylene glycol, povidone, or ethanol; and water, the composition having a pH greater than 2.5 and less than 4.

It is observed that all the disclosed midazolam formulations comprise of one or more organic solvents which might prove to be deleterious to nasal mucosa and/or need to be administered at a large quantity to deliver the required therapeutic dose. None of the prior disclosed formulations are high concentrated aqueous midazolam formulations which are primarily free of any organic solvents. There is a need for concentrated intranasal midazolam formulation with improved properties, such as for example, rapid absorption and time to peak concentration. There is also a need for intranasal compositions that improve patient compliance.

The inventors of present invention have developed a highly concentrated midazolam aqueous nasal formulation which is substantially free of organic solvents to solve the problems associated with available formulations. The formulation of present invention comprises of midazolam at high amount and pharmaceutically acceptable excipients and is suitable for nasal administration.

OBJECT OF THE INVENTION

An object of the present invention is to provide a pharmaceutical formulation comprising
high concentration of midazolam optionally with one or more pharmaceutically acceptable excipients.

Another object of the present invention is to provide a pharmaceutical formulation comprising midazolam to ensure patient compliance.

Yet another object of the present invention is to provide a pharmaceutical formulation
comprising high concentration of midazolam so that nasal administration of low volume of formulation provide adequate doses of midazolam administered efficiently and comfortably via the intranasal route.

Another object of the present invention is to provide a pharmaceutical formulation comprising midazolam with increased bioavailability and rapid peak plasma concentration.

Yet another object of the present invention is to provide a process of preparing a pharmaceutical formulation comprising midazolam and optionally with one
or more pharmaceutically acceptable excipients.

A further object of the present invention is to provide a method of treatment and/or prevention of repeated epilepsy, status epilepticus administering a pharmaceutical composition comprising midazolam and optionally with one or more pharmaceutically acceptable excipients.

Another object of the present invention is to provide a pharmaceutical composition
comprising midazolam and optionally with one or more pharmaceutically acceptable excipients for use in the treatment of repeated epilepsy, status epilepticus and inducing sedation.

The yet another object of present invention is to provide midazolam formulation suitable for administration by nasal route which is stable during storage.

Yet another object of present invention is to provide formulation in Emergency setting situation (EMS) like seizures, where patients are non-cooperative during the treatment.

SUMMARY OF THE INVENTION

According to one aspect of the present invention, there is provided a pharmaceutical
formulation comprising high concentration of midazolam and optionally one or more pharmaceutically acceptable excipients.

According to another aspect of the present invention, there is provided a process of
preparing a pharmaceutical formulation comprising midazolam and optionally one or more pharmaceutically acceptable excipients.

According to a further aspect of the present invention there is provided a method of
treating repeated epilepsy, status epilepticus, inducing sedation by administering a pharmaceutical composition comprising midazolam and optionally pharmaceutically acceptable excipients.

The invention relates to new formulations providing midazolam via the intranasal or pulmonary route. These formulations demonstrate good bioavailability (rate and extent of absorption), rapid peak plasma concentration and, do not show any toxicity/irritation towards the nasal epithelial membranes and ciliary movement. The formulation of present invention comprises high concentration of midazolam so that nasal administration of low volume of formulation provide adequate doses of midazolam efficiently and comfortably when administered via the intranasal route in a small volume.

Another aspect of present invention is to provide a stable pharmaceutical formulation comprising midazolam.

Yet another aspect of present invention is to provide formulation to ensure patient compliance especially if the patient is nervous or is a crying child or the like.

Yet another aspect of present invention is to provide formulation in Emergency setting situation (EMS) like seizures, where patients are non-cooperative during the treatment.

DETAILED DESCRIPTION

While formulating the nasal formulations and subsequently designing the dosage regimen of such formulations, the key factor is the selection of those solvents and excipients which are non-irritant to nasal mucosa in accordance with physicochemical properties of drug. Also, it is needed to administer large volumes of formulations comprising normal to low concentrations of drug to achieve desired therapeutic dose, which is not patient compliant as well it leads to wastage of formulation due to varying amounts of the composition being swallowed leading to unpleasant taste and irritation or dropping out of the nose and varying therapeutic effect.

Midazolam is water-soluble at pH less than 4 and lipid-soluble at physiological pH. Without being bound to any theory, the lower pH allows greater amounts of midazolam to be dissolved, allowing composition with higher concentrations of midazolam to be prepared which, in turn, enables smaller volumes of formulation to be administered. However, the nasal formulations having low pH are uncomfortable due to irritation to mucosa. Due to the limited solubility of midazolam, approximately up to about 30 mg/ml in water at low pH, it is difficult to formulate aqueous formulations of free base comprising high concentration of midazolam at low pH which should be stable as well as non-irritant to mucosa. The formulation should also have increased dose consistency and predictability. This, will in turn, enables one to achieve a specific therapeutic effect, as the plasma levels achieved following intranasal administration will be predictable and controllable.

The inventors of present invention after rigorous experiments have provided aqueous pharmaceutical formulation comprising midazolam in high concentration which is non-irritant to nasal mucosa and can be administered as unit dose formulation to achieve the desired therapeutic dose overcoming the disadvantages of already available formulations.

The present invention relates to pharmaceutical formulations capable of solubilizing midazolam at sufficiently high concentration to allow intranasal administration of therapeutically effective dosage forms to a patient in need thereof.

The term "pharmaceutical composition" includes nasal sprays, nasal drops, metered dose inhalers (MDI), dry powder inhalers (DPI), solutions administered by nebulizers, insufflation powders or nasal powders and the like. The pharmaceutical compositions of the present invention may be administered by any suitable methods used for delivery of the drugs to the systemic circulation.

The formulations of present invention comprises of high concentration of midazolam free base such as in range of 25 mg/mL to 90 mg/mL. In one embodiment of the invention, the concentration of midazolam free base is at least 30 mg/mL, 40 mg/ml, or at least 50 mg/mL. The midazolam free base in formulation of present invention is 3% w/w-10% w/w of the formulation. In an embodiment, the midazolam free base in formulation of present invention is 5% w/w of formulation.

In one embodiment of the invention, the midazolam included in the formulation is a salt of midazolam, such as midazolam hydrochloride, midazolam maleate or midazolam lactate. Preferably, the composition comprises midazolam hydrochloride. In an embodiment, midazolam included in the formulation is a salt and may not contain acidifying agent which functions to form salt in-situ.

The formulation of present invention comprises surfactant to solubilize the high concentration of midazolam in the formulation. Suitable surfactants which may be employed in formulation of the present invention include those which may serve to stabilize the formulation. The surfactants may also act as permeation enhancers. Because ciliary action removes drug from the absorption site, nasal membrane permeation must be fairly rapid for bioavailability to be complete. The permeation enhancer alters drug permeation through the biological membrane that acts as the barrier to absorption. Preferred surfactants include one or more ionic and/or non-ionic surfactants. Examples of suitable surfactants that may be included in formulation of present invention are, but are not limited to, oleic acid, sorbitan trioleate, lecithin, isopropylmyristate, tyloxapol, polyvinylpyrrolidone, polysorbates such as polysorbate 80 (Tween 80), vitamin E-TPGS, Tweens, Myrj, Brjs, Span 20, Span 60, Myrj, Arlacel 83, labrasol and macrogol hydroxystearates such as macrogol-15-hydroxystearate, and the like or combinations thereof. The surfactants or permeation enhancers are included in the formulation of present invention in the concentration range of 0.01-25% w/w, 0.5 to 20% w/w of formulation. In a preferred embodiment, polysorbate 80 is included in formulation of present invention at a concentration range of 0.5% to 2.5% w/w of the formulation. Incase of microemulsion formulation covered in the present invention, polysorbate is used in an amount of 15% w/w of the of formulation. In another preferred embodiment, combination of polysorbate 80 and labrasol are used in the formulation of present invention in a total amount of 0.5% to 2.5% w/w of formulation.

The ratio of midazolam and surfactant also play a critical role when the formulation comprises midazolam in high concentration. The surfactant is included in formulation of present invention in an amount such that more drug is solubilized in the unionized form and thus result in decreased amounts of insoluble free base by salt formation with acid. Additionally, the amount of surfactant used to dissolve high amount of midazolam in the formulation should not be deleterious and is acceptable under standard limits. Thus the surfactant and its ratio with midazolam is carefully chosen so that the midazolam does not precipitate while storage, remains uniformly distributed and at the same time the amount of surfactant is within the pharmaceutically acceptable limits.

The ratio of midazolam to surfactant according to present invention is from about 1:0.01 to about 1:1, preferably the ratio is 1:0.5.

The various dosage forms according to the present invention may comprise pharmaceutically acceptable nasal carrier or excipients suitable for formulating the same. The composition according to the present invention may include excipients that are well known in the art, such as, acidifying agent, pH regulators, chelating agents, preservatives, thickening agents, co-solvents, permeation enhancers, mucoadhesives, absorption enhancing agents and vehicle. The carrier(s) or excipients must be "acceptable" in the sense of being compatible with the other ingredients of the formulation and not deleterious to the recipient thereof. Such carriers are well known to those skilled in the art of pharmacology.

The formulation of present invention may contain midazolam either in the form of its free base or a pharmaceutically acceptable salt thereof. Alternatively and preferably, the formulation comprises high concentration of midazolam in free base form and is solubilized when the salt and micelles are formed in situ by reacting with acid.

The formulation further comprises other pharmaceutically acceptable excipients. The excipients, in present invention, which are used for solubilization/converting midazolam to salt or micelles are suitable acidifying agents such as inorganic, organic acids and combinations thereof. Examples of inorganic acids that can be used in the present invention are selected from, but not limited to, mineral acids, such as hydrochloric and hydrobromic acid, sulfuric acid, sulfonic acid, sulfenic acid, phosphoric acid and the combinations thereof. Examples of organic acids that can be used in the present invention are selected from, but not limited to, aliphatic carboxylic acids, such as acetic acid, ascorbic acid, carbonic acid, citric acid, butyric acid, fumaric acid, glutaric acid, glycolic acid, α-ketoglutaric acid, lactic acid, malic acid, mevalonic acid, maleic acid, malonic acid, oxalic acid, pimelic acid, propionic acid, succinic acid, tartaric acid, or tartronic acid and combinations thereof. Preferably lactic acid, hydrochloric acid is used in the present invention at a concentration of 5-15% w/w, more preferably at 7.5-12.5% w/w, most preferably at 10.5% w/w of the formulation of present invention.

The acidifying agents also act as pH regulators. The pH of pharmaceutical formulation of the present invention may be adjusted by the addition of one or more buffers or pH regulators such as pharmacologically acceptable inorganic, organic acids and base. Such pH-adjusting agents are selected from, but are not limited to, hydrochloric acid, hydrobromic acid, nitric acid, sulphuric acid, phosphoric acid, ascorbic acid, citric acid, malic acid, tartaric acid, maleic acid, succinic acid, fumaric acid, acetic acid, formic acid, propionic acid, sodium hydroxide (NaOH) and the like or combinations thereof. The compositions of the present invention preferably comprise 2N NaOH in an amount sufficient to obtain a composition pH of 3.5-3.95, more preferably a pH of 3.6-3.8. Buffers that are suitable for use in the present invention include, for example, acetate, citrate, prolamine, sodium lactate, carbonate and phosphate buffers and combinations thereof.

The compositions of the present invention may contain a pharmaceutically acceptable chelating agents. Suitable chelating agents for use in pharmaceutical compositions of the invention include editic acid (EDTA) or a salt thereof, e.g. sodium EDTA or disodium EDTA dehydrate (sodium edetate), and the like or combinations thereof. The amount of chelating agent present in the composition is from about 0.005% to 0.10% w/w of the total composition. Preferably, disodium edetate is present in formulation of present invention in an amount of 0.05 to 5% w/w, preferably 0.01% w/w of total formulation which also function as stabilizer.

The formulations of the present invention comprises at least one antimicrobial preservative in the range of 0.001% to about 0.3% by w/w of the formulation. Suitable preservatives include p-hydroxybenzoic acid ester, benzalkonium chloride, benzododecinium bromide, and the like. Suitable preservatives that can be used with the present formulations include, for example, benzyl alcohol, parabens, chlorobutanol, benzalkonium salts and combinations thereof. In a preferred embodiment, benzalkonium chloride is present in formulation of present invention at concentration of 0.01% to 0.05% w/w of formulation.

In the context of the present invention, the term solvent or vehicle means that which when added provides a formulation in which the medicament can be dissolved or dispersed. The solvent or formulation vehicle which is used in present invention is water in an amount sufficient to dissolve the midazolam free base and other excipients. In a preferred embodiment, the formulation of present invention is aqueous solution.

The formulation of present invention may or may not comprises of organic solvents such as methoxy-polyethylene glycol, polyethylene glycol, propylene glycol, ethanol and the like.

In an embodiment of present invention, the formulation of present invention does not contain ethanol as solvent.

In an embodiment, the pharmaceutical formulations of present invention having pH lower than 4, suitable to administer by nasal route comprise high concentration of midazolam free base, an acid for in-situ salt formation, polysorbate-80, buffer, chelating agent, preservative and vehicle.

In another embodiment, the pharmaceutical formulations of present invention having pH lower than 4, suitable to administer by nasal route comprise high concentration midazolam free base, may in addition further comprises mucoadhesive agents, cosurfactants and combination thereof.

The formulations of present invention are capable of demonstrating improved mucoadhesive consistency and stability. Mucoadhesive materials may be useful to provide prolonged adhesion, and so improved efficacy, of pharmaceutically active ingredients on mucosal tissue. These agents also act as thickening agents, crystal growth inhibitor to increase the nasal residence time of pharmaceutical formulation of present invention. Suitable mucoadhesive agents which can be include in formulation of present invention is selected from, but not limited to, cellulose derivatives such as cellulose ether in which the cellulose-hydroxy groups are partially etherized with lower unsaturated aliphatic alcohols and/or lower unsaturated aliphatic oxyalcohols such as methyl cellulose, carboxymethyl cellulose, hydroxypropylmethylcellulose), gelatin, polyvinylpyrrolidone, tragacanth, ethoxose, alginic acid, polyvinyl alcohol, polyacrylic acid, pectin and the like and combination thereof. The amount of mucoadhesive agents incorporated in formulation of present invention can be in the range of 0.01% to 1.0% w/w of formulation. In a preferred embodiment of present invention, hydroxypropyl methyl cellulose 6 cps can be used at an amount of 0.1% w/w of formulation.

The pharmaceutical compositions of the present invention are formulated for intranasal or
  pulmonary delivery and may therefore be administered by any suitable methods used for
  delivery of the drugs to the nasal mucosa or lungs. For example, the composition of the
  present invention may be in the form of aerosol compositions, powders, sprays, solutions, suspensions, drops, an insufflation powder or nasal powder. Such compositions may be
  administered by any conventional means, for example using a metered dose inhaler
  (MDI), a dry powder inhaler (DPI), a nebulizer, an insufflator, a powder sprayer or a
  powder inhaler.

Preferably, the pharmaceutical composition of present invention is in the form of a solution for inhalation and may be administered using, a nasal insufflator, a nasal powder sprayer or a powder inhaler. Most preferably, the pharmaceutical composition is administered using a nasal insufflator, a nasal powder sprayer or a powder inhaler.

In a preferred embodiment, the formulation of present invention is delivered via a spray device that produces a plume of spray droplets that contact the nasal mucosa. It is contemplated that the compositions can be delivered using commercially available spray devices available from, for example, Pfeiffer of America, Princeton, N.J.; Valois of America, Inc., Greenwich, Conn.; or Becton Dickinson, Franklin Lakes, N.J. Furthermore, these devices are easily operable by the patient or care giver, and leave little or no residual formulation in the device after use. Such devices can be filled with single or multi-dose amounts of the present formulation. The container holding the pharmaceutical composition and its sealing means are sterilizable. At least the parts of the device that are in contact with the pharmaceutical formulation should be constructed and assembled in a configuration that can be sterilized.

The mucosal epithelium in the nasal cavity is covered with many hair-like cilia that provide an important defense mechanism against inhaled dust, allergens and microorganisms. The normal half-time for non-absorbed substances administered to the nasal cavity is about 15 minutes due to the mucociliary clearance removing foreign particles and excess mucus toward the pharynx. For this reason, it is preferred that the absorption occurs rapidly and preferably within 0.5 to 20 minutes. However, in the current invention due to bioadhesive properties of the invention, the preferred absorption may occur within 0.5 to 300 minutes preferably between 0.5 to 60 minutes and more preferably between 0.5 and 20 minutes, for example, within 2, 3, 4, 5, 10, 15 or 20 minutes post administration. The formulation of present invention when administered via nasal route, the peak concentration of midazolam (Tmax) in the blood of the patient is achieved within 30, 25, 20, 15, 108, 5, 3 or 2 minutes after administration of the formulation.

The formulation of present invention provides a therapeutically effective dose of midazolam when the volume of formulation administered to each nostril is typically in range of 1-1000 uL, preferably not more than 700 uL, more preferably 50-150 uL per nostril, and most preferably about 100 uL/nostril.

The formulation of present invention administered by nasal route is prepared by the process describes herein. The process of preparation of formulation of present invention involves dissolving surfactant in water, dispersing midazolam in the surfactant solution, dissolving chelating agent in water and adding this solution to the solution of surfactant-midazolam. Acid is then added to the solution of midazolam, surfactant and chelating agent. Preservative is added to the solution. Finally, pH is adjusted and the solution thus obtained is filtered and stored.

The inventors of the present invention have further observed that the solubility and
  bioavailability properties of midazolam were improved by nanosizing. The formulation of present invention may be in the form of microemulsion comprising midazolam in high concentration and is capable of administration by nasal route. The microemulsion for the nasal administration of midazolam in high concentration comprising an emulsion vehicle containing water, a fatty acid ester, a hydrophilic surfactant, a polar solvent and an alcohol and optionally pharmaceutically acceptable excipients. The fatty acid ester of microemulsion of present invention is selected from, but not limited to, ethyl laurate, ethyl myristate, ethyl palmitate, ethyl linoleate, propyl isobutyhte, isopropyl laurate, isopropyl myristate, caprylic acid esters, capric acid esters and combinations thereof. Preferably Capmul® MCM (glyceryl mono-/di-caprylate/caprate) at an amount of 10% to 20% w/w of formulation is used in present invention. The hydrophilic surfactant used in formulation of present invention is selected from are those mentioned earlier and are, but not limited to, polysorbate 80, Tween 20, 40, 60 and combinations thereof. Preferably polysorbate 80 is used in formulation of present invention at an amount of 10% to 20% w/w of formulation. The microemulsion of present invention containing high midazolam concentrations are facilitated by the inclusion of polar solvent, also functioning as cosurfactant. Particularly effective cosurfactant include propylene glycol, glycerol, polyethylene glycol, povidone and ethanol, or combinations thereof. The inclusion of cosurfactant not only enables the formation of formulation, but also allows that solution to have a high midazolam concentration. Preferably, the cosurfactant included in present invention is propylene glycol, ethanol or combination thereof at an amount of 5% to 50% w/w of the formulation. The microemulsion of present invention may also comprises of chelating agent as mentioned earlier such as disodium edetate in an amount of 0.01% to 1% w/w of the formulation. The pH of the microemulsion of the present invention is maintained at 5 to 8, preferably 6 to 7, most preferably 6.4. In an embodiment of present invention, the amount of fatty acid ester is less than the amount of water. In another embodiment, the amount of polar solvent is greater than the hydophilic surfactant. The microemulsion of present invention could be delivered to the nasal cavity as drops, mists, aerosols, instillations, by use of pipetor, special devices, evaporators, vaporizators and such. The globule size of the particles in the microemulsion of present invention was preferably less than 150 nm, more preferably less than 100 nm and most preferably less than 80 nm. The microemulsion of present invention is prepared by the process known in the art. The process of preparation involves dissolving surfactant in polar solvents, adding midazolam to the solution, adding fatty ester to the surfactant solution, adding chelating agent solution to the drug solution, making up the volume with water, filtering and storing the microemulsion.

The present invention also provides a method of treating repeated epilepsy, status epilepticus and inducing sedation by administering the pharmaceutical formulation of present invention comprising midazolam.

The present invention also provides the pharmaceutical formulation comprising midazolam of the present invention for use in treatment of repeated epilepsy, status epilepticus and inducing sedation.

The present invention also provides the use of a pharmaceutical formulation comprising midazolam of the present invention in the manufacture of a medicament for treatment of repeated epilepsy, status epilepticus and inducing sedation.

The present invention also provides a method of treating repeated epilepsy, status epilepticus and inducing sedation, wherein the method comprises administering a daily dose of from about 2 mg/kg of body weight to about 9 mg/kg of body weight to a patient.

The following examples are for the purpose of illustration of the invention only and are not intended in any way to limit the scope of the present invention.

Example 1: Midazolam Nasal Solution

TABLE 1

Composition of nasal solution

| Ingredients | Quantity (% w/w) |
| --- | --- |
| Midazolam | 5 |
| Polysorbate 80 | 2.5 |
| Lactic acid | 10.5 |
| 2N Sodium hydroxide solution | q.s to pH 3.2 |
| Disodium edetate | 0.1 |
| Benzalkonium chloride | 0.02 |
| Purified water | q.s |
| Final pH target after adjustment | 3.2 |

Process of Preparation:
1. Water was heated till 90° on magnetic stirrer and then cooled by purging nitrogen.
2. Polysorbate 80 was dissolved in some amount of water from step 1 and stirred for some time.
3. Dispersed midazolam in the polysorbate 80 solution obtained in step 2 and white suspension was obtained.
4. Dissolved separately disodium edetate in water and added to suspension of step 3 and stirred for some time.
5. Added gradually some quantity of lactic acid to solution of step 4 under stirring until clear solution is obtained.
6. Added benzalkonium chloride to the clear solution obtained in step 5 under stirring.
7. Adjusted the pH of solution obtained in step 6 to 3.2 using 1N sodium hydroxide solution under stirring, made up the volume by remaining amount of water and filtered the bulk through 0.22 micron membrane (PES) using vacuum filter assembly.

Example 2: Midazolam Nasal Solution

TABLE 2

Composition of nasal solution

| Ingredients | Quantity (% w/w) |
| --- | --- |
| Midazolam | 5 |
| Caprylocaproyl Polyoxyl-8 glycerides | 2 |
| Polysorbate 80 | 0.5 |
| Lactic acid | 10.5 |
| Disodium edetate | 0.1 |
| Benzalkonium chloride | 0.02 |
| Hydroxypropylmethyl cellulose 6 cps | 0.1 |
| 2N sodium hydroxide solution | q.s to pH 3.2 |
| Purified water | q.s |
| Final pH after adjustment | 3.2 |

Process of preparation
1. Water was heated till 90° on magnetic stirrer and then cooled by purging nitrogen.
2. Polysorbate 80 was dissolved in some amount of water from step 1 and stirred for some time.
3. Dispersed midazolam in the polysorbate 80 solution obtained in step 2 and white suspension was obtained.
4. Dissolved separately disodium edetate in water and added to suspension of step 3 and stirred for some time.
5. Added gradually some quantity of lactic acid to solution of step 4 under stirring until clear solution is obtained.

6. Added Caprylocaproyl Polyoxyl-8 glycerides, hydroxypropylmethyl cellulose and benzalkonium chloride to the clear solution obtained in step 5 under stirring.
7. Adjusted the pH of solution obtained in step 6 to 3.2 using 1N sodium hydroxide solution under stirring, made up the volume by remaining amount of water and filtered the bulk through 0.22 micron membrane (PES) using vacuum filter assembly.

Example 3: Midazolam Nasal Microemulsion

TABLE 3 composition of microemulsion

| Ingredients | Quantity (% w/w) |
| --- | --- |
| Midazolam | 5 |
| Polysorbate 80 | 15 |
| Ethanol | 7 |
| Propylene glycol | 30 |
| Glyceryl Caprylate | 15 |
| Purified water | 28 |
| Disodium edetate | 0.1 |
| Initial pH | 6.4 |

Process of Preparation:
1. Mixed polysorbate 80, propylene glycol and ethanol and stirred for 15 min to
    obtain yellow colored hazy dispersion.
2. Added midazolam in the dispersion of step 1 to obtain clear and deep yellow
    dispersion obtained.
3. Added Glyceryl Caprylate to dispersion of step 2 to obtain clear and deep yellow vehicle with very few drug particles remained suspended in
    the vehicle.
4. Separately dissolved some quantity of Disodium edetate in water and added this
    solution to vehicle of step 3 to obtain clear and deep yellow colored dispersion.
5. The volume was made up with water, filtered using 0.2 micron PES membrane
    filter and filled in 5 ml flint glass vial.

Example: 4 (Preclinical Studies)

The objective of this study was to assess the single dose pharmacokinetic profile of
  Midazolam solution formulations of present invention in male Sprague Dawley rats following single intravenous injection and intranasal administration at dose of 2 mg/kg
  body weight.
  The study design are as follows:

TABLE 4

| Group | Treatment | Dose | Route | Dose volume | Strength |
| --- | --- | --- | --- | --- | --- |
| G1 | Control (normal saline) | — | IN | 10 μL/rat (0.04 mL/kg) | 0 |
| G2 | Injection | 2 mg/kg | IV bolus | 100 μL/rat (0.4 mL/kg) | 5.0 |
| G3 | Intranasal solution of example 1 | 2 mg/kg | Intranasal route | 10 μL/rat (0.04 mL/kg) | 50.00 |
| G4 | Intranasal solution of example 2 | 2 mg/kg | Intranasal route | 10 μL/rat (0.04 mL/kg) | 50.00 |
| G5 | Microemulsion of example 3 | 2 mg/kg | Intranasal route | 10 μL/rat (0.04 mL/kg) | 50.00 |

Method:
  The pharmacokinetics of midazolam formulations was assessed by intravenous and
  intranasal administration at dose of 2 mg/kg body weight using male Sprague Dawley rats in each group. Rats from group 1 received normal saline which will be considered as control group, group 2 received intravenous injection of reference item solution through marginal ear vein. Liquid formulations of test formulations were administered intranasally in group 3, 4 and 5 animals respectively. For intranasal
  administration, rats were placed in restrainer and a light anesthesia was induced using
  isoflurane. After induction of anesthesia, all animals were held in a supine position during administration and for 1 min after drug administration. Blood samples were collected from group 2 at pre-dose, 0.083, 0.25, 0.5, 1.0, 2.0 and 4.0 h post dose while in group 3 to 5 blood was collected at pre-dose, 0.25, 0.5, 1.0, 2.0 and 4.0 h post dose. Plasma was obtained by centrifuging the blood samples at 5000 rpm for 10 min under 2-4° C. Separated plasma samples were analyzed for the midazolam levels by LC-MS/MS method
  Frequency of administration: Once daily dosing for 7 continuous days (all groups)
    Intravenous administration: Once daily dosing for 7 continuous days of Intravenous (bolus) administered through tail vein (on Day 1 and 7) or jugular vein cannula.
    Intranasal administration: Rats will be anesthetized with isoflurane (4% approximately for 3 minutes) and placed in supine position. A 15 mm PE10 tubing connected to PESO will be attached to Hamilton syringe and will be used for intranasal administration of test formulation. Formulation will be taken from the container with syringe assembly and will be administered to both nostrils (equal volumes in each nostril) for group 1, 3, 4 and 5

Results:

The following is a summary of the pharmacokinetic parameters in G2, G3, G4 and G5:

TABLE 5

Midazolam
[Geometric Mean parameters]

| PK Parameters | G-2 (IV) Day 1 | G-2 (IV) Day 7 | G-3 (IN) Day 1 | G-3 (IN) Day 7 | G-4 (IN) Day 1 | G-4 (IN) Day 7 | G-5 (IN) Day 1 | G-5 (IN) Day 7 |
|---|---|---|---|---|---|---|---|---|
| C0(IV) or Cmax(IN) (ng/ml) | 1563 | 1607 | 1399 | 964 | 1427.1 | 1228.0 | 767.2 | 451.4 |
| Cmin (ng/ml) | — | 25 | — | 0 | — | 0 | — | 0 |
| Cavg (ng/ml) | — | 33 | — | 24 | — | 29.7 | — | 11.7 |
| Tmax (h) – Median | — | — | 0.13 | 0.08 | 0.08 | 0.08 | 0.13 | 0.08 |
| AUClast (hr * ng/ml) | 633 | 843 | 796 | 556 | 750 | 673 | 476 | 260 |
| AUCINF (hr * ng/ml) | 652 | 803 | 810 | 566 | 779 | 717 | 494 | 273 |
| t1/2 (h) | 0.5 | 1.6 | 0.5 | 0.5 | 0.52 | 0.64 | 0.44 | 0.44 |
| Kel (1/hr) | 1.5 | 0.4 | 1.5 | 1.5 | 1.33 | 1.00 | 1.57 | 1.59 |
| Vzobs(IV) or Vz/F(IN) (L) | 2 | 5 | 2 | 2 | 1.9 | 2.8 | 2.6 | 4.6 |
| CLobs(IV) or CL/F(IN) (mL/min) | 51 | 32 | 41 | 59 | 43 | 46 | 67 | 122 |
| Absolute bioavailability (F) | — | — | 124 | — | 117 | — | 74 | — |

Conclusion:
- Median $T_{max}$ of Group 3(IN) and Group 5 (IN) were found to be range of 5 to 7.5 minutes on day 1 and day 7. However, $T_{max}$ of group 4 (IN) was found to be 5 minutes on day 1 and day 7.
- Formulation group 3 and group 4 have higher bioavailability compared to group 5.
- Intravenous administration of MTF injection (IV) showed comparable exposure on day 1 and day 7.
- Indicate no accumulation in repeated dosing in Intranasal groups however, exposures were reduced by 30, 10 and 40%, respectively.
- The elimination rate constant and half-life of in all the intranasal dose formulation was found to be comparable on day 1 and day 7.
- Low to moderate variability was observed in all test groups on day 1 and day 7 (<30-70% CV most of the time points).

Example 5: Midazolam Nasal Solution

TABLE 6 composition of nasal solution

| Ingredients | Quantity (% w/w) |
|---|---|
| Midazolam | 5 |
| Polysorbate 80 | 2.5 |
| Propylene glycol | 20.0 |
| Polyethylene glycol 400 | 20.0 |
| Ethanol | 7.0 |
| Disodium edetate | 0.01 |
| Purified water | q.s to 100 |
| Hydrochloric acid (5N) | q.s. to 3.5 |
| Midazolam | 5 |

Process of Preparation:

Mixed propylene glycol, polyethylene glycol 400, ethanol and polysorbate 80, added acidified water to it. Added midazolam to the solution. Separately dissolved some quantity of Disodium edetate in water and added this midazolam solution to vehicle to obtain clear and deep yellow colored dispersion. The volume was made up with water, filtered using 0.2 micron PES membrane filter and filled in 5 ml flint glass vial.

Example 6: Midazolam Formulation with Glycofural

TABLE 7

| Ingredients | Quantity |
|---|---|
| Midazolam | 5 |
| Polysorbate 80 | 2.5 |
| Glycofurol | 20.0 |
| Disodium edetate | 0.01 |
| Purified water | q.s to 100 |
| Hydrochloric acid (5N) | q.s. to 3.5 |

Process of Preparation:

Mixed polysorbate 80 and glycofural and prepared a solution. Added midazolam and HCl and water to the solution. Separately dissolved some quantity of Disodium edetate in water and added this midazolam solution to vehicle to obtain clear and deep yellow colored dispersion. The volume was made up with water, filtered using 0.2 micron PES membrane filter and filled in 5 ml flint glass vial.

Example 7: PK Study Design

A single dose comparative pharmacokinetic study of Midazolam following intravenous and intranasal administration in Male sprague Dawley Rats was performed with following protocol:

TABLE 8

| Group | Treatment | Dose (mg/kg) | Strength (mg/mL) | Dose Vol | Animal Id's |
|---|---|---|---|---|---|
| 6 | MTF Intravenous Injection | 2 | 5 | 100 μL/rat | 1 to 8 |
| 7 | T1(Nasal Spray/IN formulation of example 5 | 2 | 50 | 10 μL/rat | 9 to 18 |
| 8 | T2 (Nasal Spray/IN formulation of example 6 | 2 | 50 | 10 μL/rat | 19 to 28 |

PK Study Results:

TABLE 9

Midazolam mean plasma concentrations (ng/mL)

| Time (hrs) | Group-6: MTF Injection/IV bolus | Group-7: Nasal Spray/IN formulation of example 5 | Group-8: Nasal Spray/IN formulation of example 6 |
| --- | --- | --- | --- |
| 0 | 0.00 | 0.00 | 0.00 |
| 0.08 | 1125.63 | 1995.00 | 1792.00 |
| 0.16 | 733.75 | 1285.10 | 1290.40 |
| 0.33 | 518.00 | 757.10 | 882.60 |
| 0.5 | 412.25 | 503.10 | 641.40 |
| 0.75 | 288.15 | 382.10 | 389.60 |
| 1 | 213.71 | 215.10 | 252.30 |
| 1.5 | 106.04 | 118.50 | 129.20 |
| 2 | 59.55 | 60.33 | 50.19 |
| 3 | 10.39 | 14.62 | 9.87 |

Figure 1:
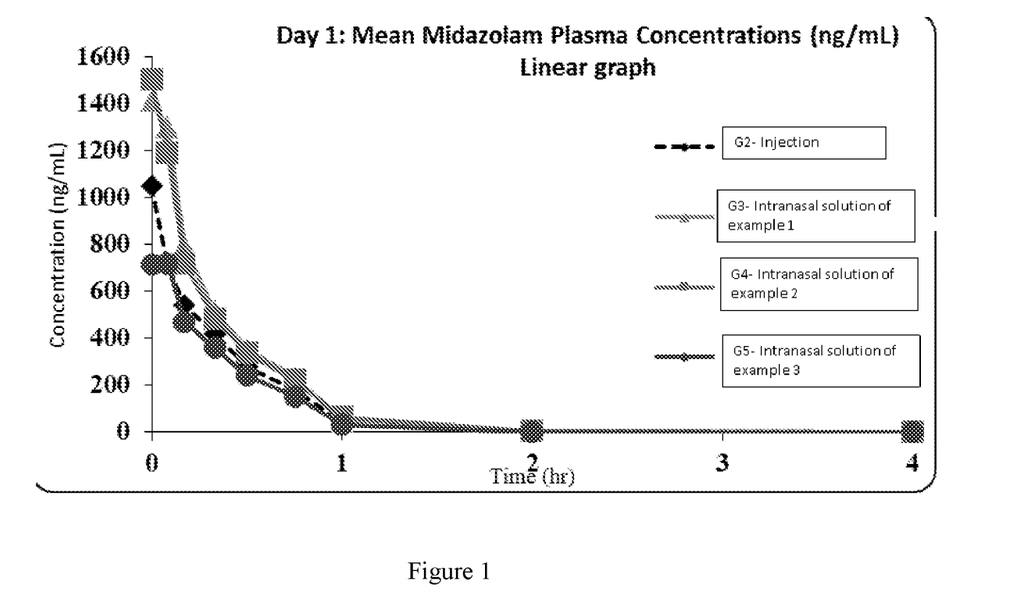
FIG. 1: Midazolam plasma concentration graph after administration of formulation in Group 2, 3, 4 and 5 on day 1
Figure 2:
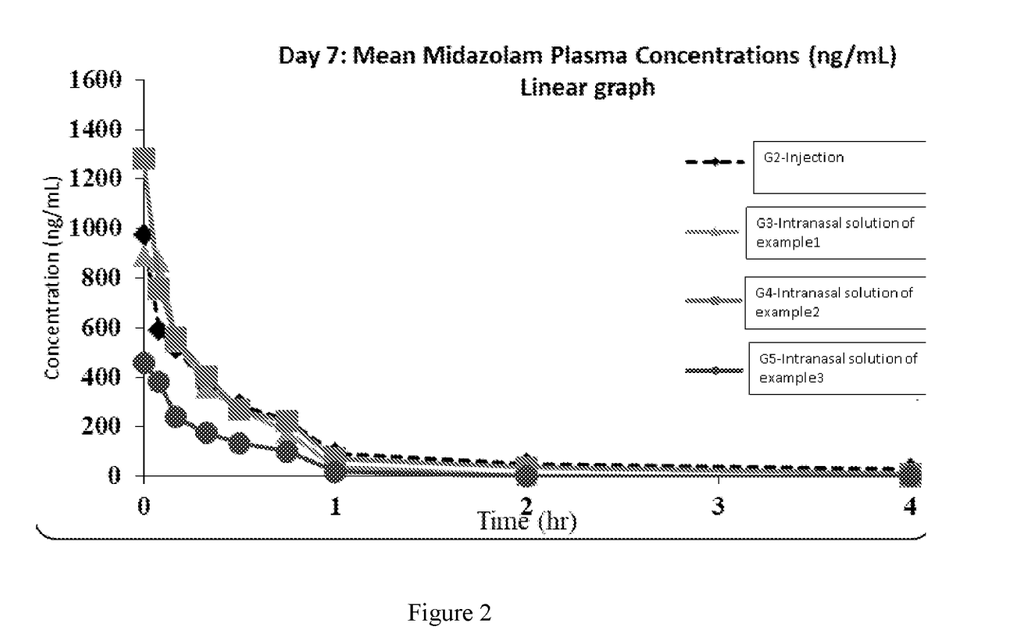
FIG. 2: Midazolam plasma concentration graph after administration of formulation in Group 2, 3, 4 and 5 on day 7
Figure 3:
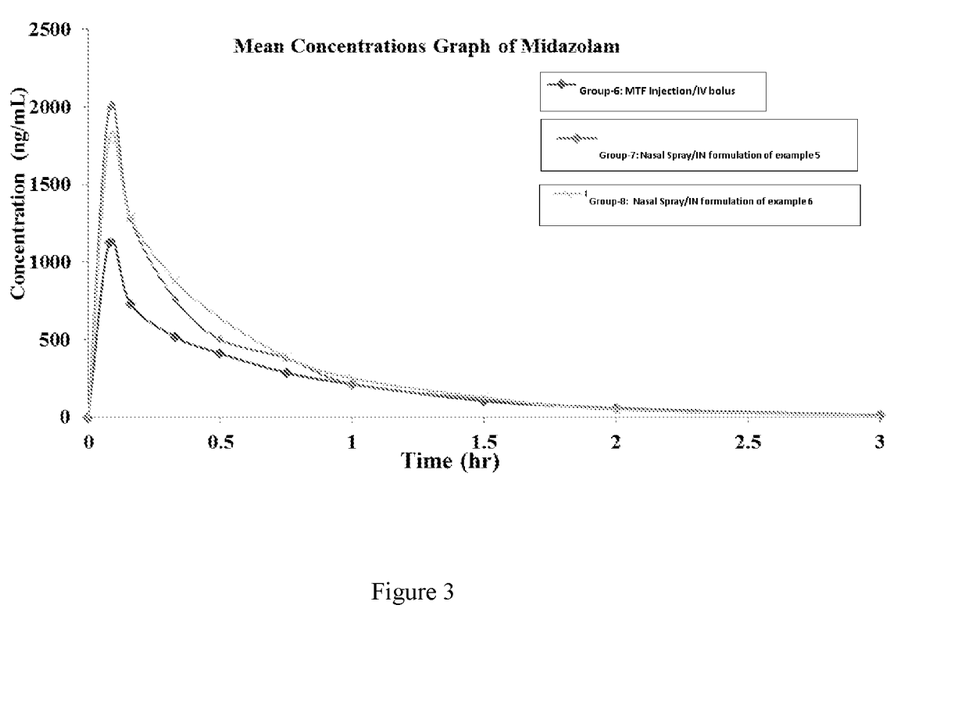
FIG. 3: Mean midazolam concentration graphs of group 6, 7 and 8

The results of above Pk study is shown in FIG. 3. It is observed from the study that midazolam is absorbed rapidly into systemic circulation after intranasal delivery and both the test formulations of example 5 and example 6 showed similar bioavailability profile after intranasal administration in compare to IV formulation. Further, both intranasal test formulation showed similar $C_{max}$ and AUC profile. Formulations of example 5 and 6 showed 0.96 and 0.94 times of $C_{max}$ in compare to Intravenous route. On contrary, formulations of 5 and 6 showed 1.1 and 1.2 times exposure in compare to Parenteral route (as per geometric mean). Also, absolute Bioavailability of formulations of example 5 and 6 is 98% and 104% (As per Geometric mean), in compare to intravenous formulation. Thus, it is concluded, midazolam intranasal instillation showed similar PK profile in compare to Parenteral route in male rats.

Example 8: Midazolam Nasal Solution

TABLE 10

| Ingredients | Quantity (%w/w) |
| --- | --- |
| Midazolam | 5 |
| Polysorbate 80 | 2.5 |
| Propylene glycol | 20.0 |
| Polyethylene glycol 400 | 20.0 |
| Disodium edetate | 0.01 |
| Purified water | q.s to 100 |
| Hydrochloric acid (5N) | q.s. to 3.5 |

Process of Preparation:

Mixed polysorbate 80, polyethylene glycol and polyethylene glycol and prepared a solution. Added midazolam and HCl and water to the solution. Separately dissolved some quantity of Disodium edetate in water and added this midazolam solution to vehicle to obtain clear and deep yellow colored dispersion. The volume was made up with water, filtered using 0.2 micron PES membrane filter and filled in 5 ml flint glass vial.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "a propellant" includes a single propellant as well as two or more different propellants; reference to a "solvent" refers to a single solvent or to combinations of two or more solvents, and the like.

We claim:

1. A pharmaceutical formulation in the form of an aqueous solution for intranasal administration comprising midazolam at a concentration of 5% w/w of the formulation, polysorbate 80 as a surfactant at a concentration of 2.5% w/w of the formulation and pharmaceutically acceptable excipients.

2. The formulation as claimed in claim 1, wherein midazolam is used in the form of a free base.

3. The formulation of claim 1, wherein the formulation comprises a pH adjusting agent selected from hydrochloric acid, hydrobromic acid, sulfuric acid, sulfonic acid, sulfenic acid, phosphoric acid, acetic acid, ascorbic acid, carbonic acid, citric acid, butyric acid, fumaric acid, glutaric acid, glycolic acid, α-ketoglutaric acid, lactic acid, malic acid, mevalonic acid, maleic acid, malonic acid, oxalic acid, pimelic acid, propionic acid, succinic acid, tartaric acid, or tartronic acid, sodium hydroxide (NaOH), acetate, citrate, prolamine, sodium lactate, carbonate and phosphate buffers and combinations thereof.

4. The formulation of claim 3, wherein the pH adjusting agent is hydrochloric acid, lactic acid or combination thereof.

5. The formulation of claim 1, wherein a pH adjusting agent is present in an amount of from 7.5% to 12.5% w/w of formulation.

6. The formulation of claim 1, wherein the formulation comprises of chelating agent selected from sodium EDTA or disodium edetate or combinations thereof in amount of from 0.005% to 0.10% w/w of the total formulation.

7. The formulation of claim 6, wherein the chelating agent is disodium edetate at an amount of 0.1% w/w of total formulation.

8. The formulation of claim 1, wherein the formulation comprises of antimicrobial preservative selected from p-hydroxybenzoic acid ester, benzalkonium chloride, benzododecinium bromide, and the combination thereof in an amount of from 0.001% to 0.3% by w/w of the formulation.

9. The formulation of claim 8, wherein the preservative is benzalkonium chloride at an amount of 0.02% w/w of formulation.

10. The formulation of claim 1, wherein the formulation comprises a solvent system selected from water, methoxypolyethylene glycol, polyethylene glycol, propylene glycol, ethanol and the combination thereof.

11. The formulation of claim 10, wherein the solvent system does not contain ethanol.

12. The formulation of claim 1, wherein the aqueous solution has a pH of less than 4.

13. The formulation of claim 1, wherein a therapeutically effective dose of midazolam is achieved when the volume of formulation administered to each nostril is 50-150 uL per nostril.

\* \* \* \* \*

UNITED STATES PATENT AND TRADEMARK OFFICE
CERTIFICATE OF CORRECTION

| | | |
|---|---|---|
| PATENT NO. | : 12,324,811 B2 | Page 1 of 1 |
| APPLICATION NO. | : 17/415966 | |
| DATED | : June 10, 2025 | |
| INVENTOR(S) | : Geena Malhotra et al. | |

It is certified that error appears in the above-identified patent and that said Letters Patent is hereby corrected as shown below:

In the Specification

In Column 1: Replace the structural formula with the following:

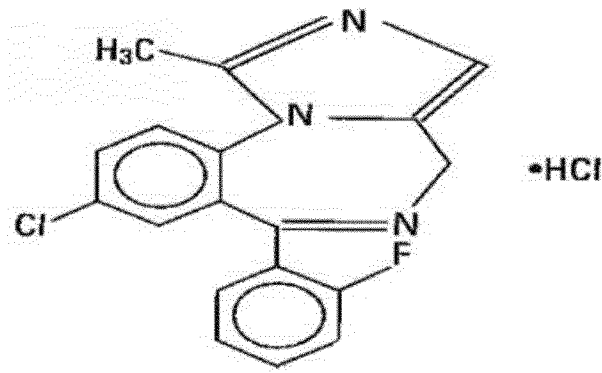

Signed and Sealed this
Twenty-sixth Day of August, 2025

Coke Morgan Stewart
*Acting Director of the United States Patent and Trademark Office*